(12) United States Patent
Uchiyama et al.

(10) Patent No.: US 11,442,182 B2
(45) Date of Patent: Sep. 13, 2022

(54) TIME SYNCHRONIZATION SYSTEM, METHOD OF CONTROLLING TIME SYNCHRONIZATION SYSTEM, AND RADIATION IMAGING SYSTEM

(71) Applicant: CANON KABUSHIKI KAISHA, Tokyo (JP)

(72) Inventors: Akehiko Uchiyama, Kawasaki (JP); Tadahiko Iijima, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 162 days.

(21) Appl. No.: 16/720,516

(22) Filed: Dec. 19, 2019

(65) Prior Publication Data

US 2020/0209409 A1    Jul. 2, 2020

(30) Foreign Application Priority Data

Dec. 27, 2018   (JP) .............................. JP2018-245378

(51) Int. Cl.
*G01T 1/17* (2006.01)
*H04J 3/06* (2006.01)
(Continued)

(52) U.S. Cl.
CPC .............. *G01T 1/17* (2013.01); *H04J 3/0638* (2013.01); *H04L 67/12* (2013.01); *H04L 67/42* (2013.01)

(58) Field of Classification Search
CPC ............ H04W 84/12; H04W 74/0808; H04W 74/0816; H04W 72/0446; H04W 72/04;
(Continued)

(56) References Cited

U.S. PATENT DOCUMENTS 6,246,702 B1 * 6/2001 Fellman .............. H04L 12/6418
                                                          370/354
2001/0033579 A1 * 10/2001 Nelson, Jr. .......... H04L 12/5602
                                                          370/447
(Continued)

FOREIGN PATENT DOCUMENTS

CN      107231701 A      10/2017
JP      2003008593 A      1/2003
(Continued)

OTHER PUBLICATIONS

Extended European Search Report issued by the European Patent Office dated Apr. 30, 2020 in corresponding European Patent Application No. 19215010.0.

*Primary Examiner* — Michael A Keller
*Assistant Examiner* — Thao D Duong
(74) *Attorney, Agent, or Firm* — Carter, DeLuca & Farrell LLP (57) ABSTRACT

A time synchronization system includes at least one time server and a plurality of time clients connected to each other via a network. The time client comprises: a communication unit configured to obtain time information of the time server by transmitting/receiving messages to/from the time server; and a time count control unit configured to synchronize time information of an internal timepiece with time information of the time server. The time count control unit controls transmission of the messages by adjusting transmission intervals of the messages to irregular intervals.

15 Claims, 7 Drawing Sheets

(51) Int. Cl.
*H04L 29/08* (2006.01)
*H04L 29/06* (2006.01)
*H04L 67/12* (2022.01)
*H04L 67/01* (2022.01)

(58) Field of Classification Search
CPC . H04W 74/085; H04B 10/116; H04B 10/516; H04B 17/318; H04B 10/11; H04B 10/1143
See application file for complete search history.

(56) References Cited

U.S. PATENT DOCUMENTS

| | | | |
|---|---|---|---|
| 2013/0010774 A1* | 1/2013 | Subramanian | H04W 74/0808 370/338 |
| 2013/0053705 A1 | 2/2013 | Kim et al. | |
| 2013/0195251 A1 | 8/2013 | Saigusa et al. | |
| 2014/0098706 A1 | 4/2014 | Maruyama et al. | |
| 2015/0085836 A1* | 3/2015 | Kang | H04W 74/0808 370/336 |
| 2015/0289163 A1* | 10/2015 | Mineta | H04J 13/16 370/320 |
| 2015/0382374 A1* | 12/2015 | Bhorkar | H04W 72/0453 370/330 |
| 2016/0192359 A1* | 6/2016 | Anouar | H04L 5/0055 370/336 |

FOREIGN PATENT DOCUMENTS

| | | |
|---|---|---|
| JP | 2007158425 A | 6/2007 |
| JP | 2010081960 A | 4/2010 |
| JP | 2016136652 A | 7/2016 |
| WO | 2018186275 A1 | 10/2018 |

* cited by examiner

TIME SYNCHRONIZATION SYSTEM, METHOD OF CONTROLLING TIME SYNCHRONIZATION SYSTEM, AND RADIATION IMAGING SYSTEM

BACKGROUND OF THE INVENTION

Field of the Invention

The present invention relates to a time synchronization system, a method of controlling a time synchronization system, and a radiation imaging system.

Description of the Related Art

A radiation imaging apparatus and a radiation imaging system in which a radiation image obtained from radiation emitted from a radiation generating apparatus and transmitted through a subject is converted into a digital image, and the digital image undergoes image processing to obtain sharp radiation image data are commercially available.

In such a radiation imaging apparatus, a two-dimensional solid-stage image sensor is generally used as a radiation detector. The radiation detector converts the emitted radiation into charges, accumulates the charges in a capacitor, and repeats the readout and reset operation of the accumulated charges. In an image sensor without an electronic shutter, when radiation irradiation is made on the image sensor at the time of charge readout and reset operation, charges nonrelated to the radiation imaging are superimposed on the radiation image, thereby degrading the quality of the radiation image.

Accordingly, a radiation imaging system is required to establish synchronization between the operation timing of a radiation detector in a radiation imaging apparatus and the irradiation timing of a radiation generating apparatus.

Japanese Patent Laid-Open No. 2010-081960 discloses a radiation imaging system including a radiation source control apparatus having a first timer and a radiation imaging apparatus having a second timer that is synchronized with the first timer by the communication of time information.

The arrangement disclosed in Japanese Patent Laid-Open No. 2010-081960 is premised on a system arrangement in which a radiation imaging system includes one each of a radiation imaging apparatus as a time client and a radiation source control apparatus as a time server. Accordingly, time synchronization may not be established in a system arrangement configured to use a plurality of radiation imaging apparatuses (time clients) while flexibly switching them or to obtain a long image by simultaneously and synchronously operating the radiation imaging apparatuses.

In consideration of the above problem, the present invention provides a time synchronization technique that can more accurately perform time synchronization.

SUMMARY OF THE INVENTION

According to one aspect of the present invention, there is provided a time synchronization system including at least one time server and a plurality of time clients connected to each other via a network, the time client comprising: a communication unit configured to obtain time information of the time server by transmitting/receiving messages to/from the time server; and a time count control unit configured to synchronize time information of an internal timepiece with time information of the time server, wherein the time count control unit controls transmission of the messages by adjusting transmission intervals of the messages to irregular intervals.

According to another aspect of the present invention, there is provided a time synchronization system including at least one time server and a plurality of time clients connected to each other via a network, the time server comprising: a communication unit configured to transmit time information of an internal timepiece upon transmitting/receiving messages to/from the plurality of time clients; and a time count control unit configured to output, when a plurality of messages have arrived within a predetermined time, via the communication unit, collision estimation information generated with respect to a message from a time client which has arrived later, and the time client comprising a time count control unit configured to synchronize time information of an internal timepiece with time information of the time server which is obtained by transmitting a message, and wherein the time count control unit of the time client adjusts transmission intervals of the messages to irregular intervals and controls transmission of the messages upon receiving the collision estimation information.

According to another aspect of the present invention, there is provided a radiation imaging system including a plurality of radiation imaging apparatuses functioning as time clients and an irradiation control apparatus functioning as a time server and configured to control a radiation generating apparatus, the radiation imaging apparatus comprising: a communication unit configured to obtain time information of the irradiation control apparatus by transmitting/receiving messages to/from the time server; and a time count control unit configured to synchronize time information of an internal timepiece with time information of the irradiation control apparatus, and wherein the time count control unit controls transmission of the messages by adjusting transmission intervals of the messages to irregular intervals.

According to still another aspect of the present invention, there is provided a radiation imaging system including a plurality of radiation imaging apparatuses functioning as time clients and an irradiation control apparatus functioning as a time server and configured to control a radiation generating apparatus, the irradiation control apparatus comprising: a communication unit configured to transmit time information of an internal timepiece by transmitting/receiving messages to/from the plurality of radiation imaging apparatuses; and a time count control unit configured to output, when a plurality of messages have arrived within a predetermined time, via the communication unit, collision estimation information generated with respect to a message from a radiation imaging apparatus which has arrived later, and the radiation imaging apparatus comprising a time count control unit configured to synchronize time information of an internal timepiece with time information of the irradiation control apparatus which is obtained by transmitting a message, and wherein the time count control unit of the radiation imaging apparatus adjusts transmission intervals of the messages to irregular intervals and controls transmission of the messages upon receiving the collision estimation information.

According to yet another aspect of the present invention, there is provided a method of controlling a time synchronization system including at least one time server and a plurality of time clients connected to each other via a network, the method comprising: in the time client, a communication step of obtaining time information of the time server by transmitting/receiving messages to/from the time server; and a time count control step of synchronizing time information of an internal timepiece with time information of the time server, wherein in the time count control, transmission of the messages is controlled by adjusting transmission intervals of the messages to irregular intervals.

According to still yet another aspect of the present invention, there is provided a method of controlling a time synchronization system including at least one time server and a plurality of time clients connected to each other via a network, the method comprising: in the time server, a communication step of transmitting time information of an internal timepiece upon transmitting/receiving messages to/from the plurality of time clients; and a time count control step of, when a plurality of messages have arrived within a predetermined time, outputting, via a communication unit, collision estimation information generated with respect to a message from a time client which has arrived later, and the method comprising, in the time client, a time count control step of synchronizing time information of an internal timepiece with time information of the time server, wherein in the time count control step of the time client, transmission intervals of the messages are adjusted to irregular intervals and transmission of the messages is controlled upon reception of the collision estimation information.

The present invention can provide a time synchronization technique that can more accurately perform time synchronization.

Further features of the present invention will become apparent from the following description of exemplary embodiments (with reference to the attached drawings).

DESCRIPTION OF THE EMBODIMENTS

Embodiments of the present invention will be described in detail with reference to the accompanying drawings. Note that details of sizes and structures shown in the respective embodiments are not limited to the specification and drawings. Note that radiation includes an α-ray, a β-ray, a γ-ray, and various kinds of particle beams.

First Embodiment

Figure 1:
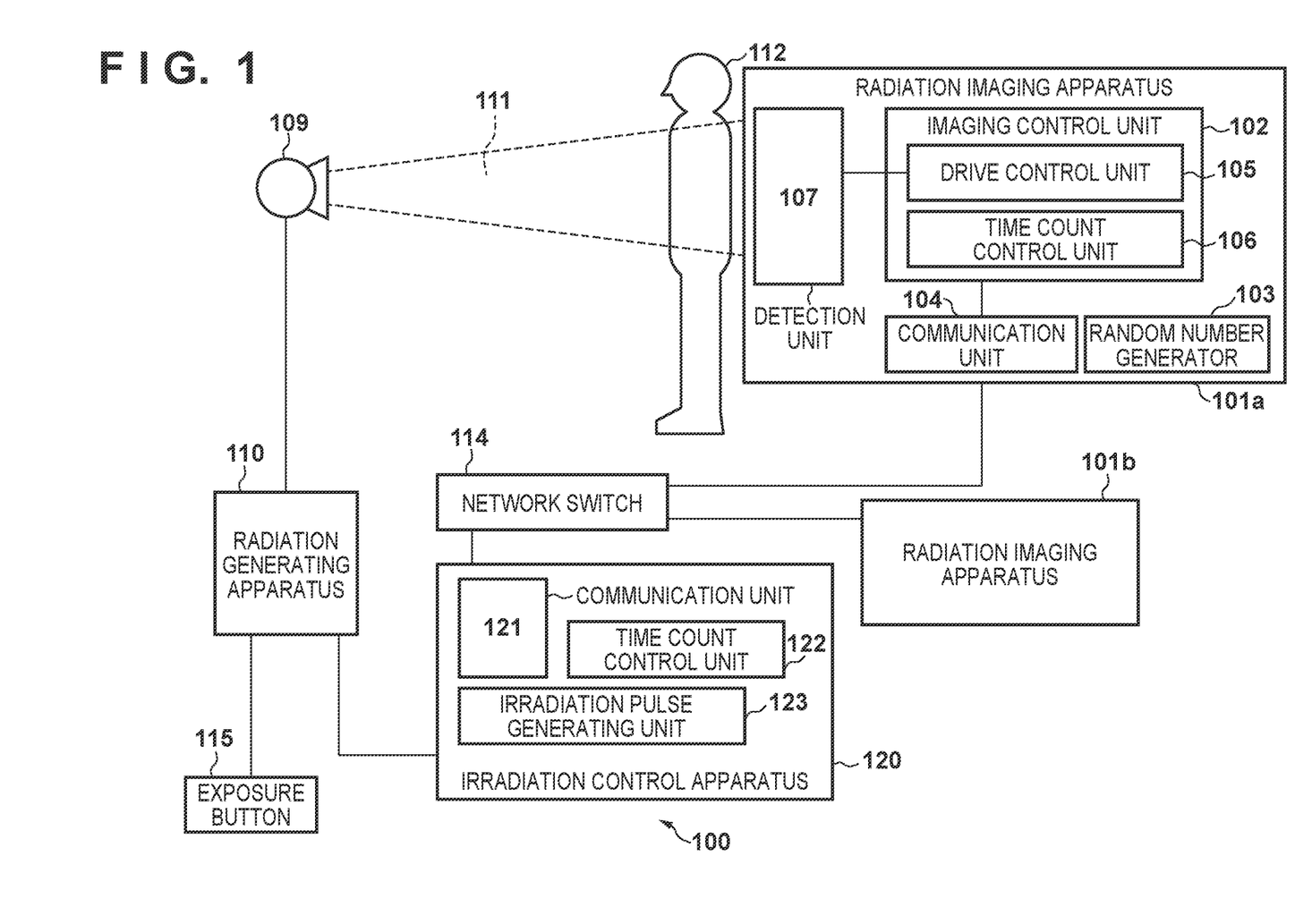
FIG. 1 is a block diagram showing an example of the arrangement of a radiation imaging system according to the first embodiment.

FIG. 1 shows an example of the arrangement of a radiation imaging system 100 according to the first embodiment of the present invention. The radiation imaging system 100 includes a plurality of radiation imaging apparatuses 101a and 101b, a radiation generating apparatus 110, and an irradiation control apparatus 120 that controls the radiation generating apparatus 110. The radiation imaging system 100 has a time synchronization system including at least the irradiation control apparatus 120 functioning as one time server and the radiation imaging apparatuses 101a and 101b functioning as a plurality of time clients.

The operator can set operation conditions for the system by using an operation device and a display device (which are not shown). The set information is transmitted to the radiation imaging apparatuses 101a and 101b and the irradiation control apparatus 120 via a network. When the operator presses an exposure button 115, the irradiation control apparatus 120 and the radiation imaging apparatuses 101a and 101b exchange messages concerning the start of an imaging operation. Subsequently, the radiation generating apparatus 110 emits radiation. After the radiation emitted by the radiation generating apparatus 110 is transmitted through a subject 112, the radiation imaging apparatuses 101a and 101b obtain images. The radiation imaging apparatuses 101a and 101b transfer the obtained images to an image processing apparatus (not shown). The images are then output to various types of display apparatuses.

The irradiation control apparatus 120 includes a communication unit 121, a time count control unit 122, and an irradiation pulse generating unit 123. The communication unit 121 transmits the time information of an internal timepiece upon transmission/reception of messages between a plurality of radiation imaging apparatuses (time clients). At the time of imaging, the irradiation control apparatus 120 outputs, to the radiation generating apparatus 110, a signal (control signal) for timing control of irradiation with radiation, which is generated by the irradiation pulse generating unit 123 with reference to the time count control unit 122, upon completion of message exchange concerning the start of an imaging operation between the radiation imaging apparatuses 101a and 101b.

The radiation generating apparatus 110 includes a tube and an exposure field aperture. The radiation generating apparatus 110 generates radiation in the form of pulses or continuously based on a timing signal from the irradiation control apparatus 120. The radiation imaging apparatuses 101a and 101b synchronized with the irradiation timing image the radiation emitted from the radiation generating apparatus 110.

The radiation imaging apparatus 101a includes a detection unit 107 having a two-dimensional array of pixels for converting radiation into electrical signals, an imaging control unit 102, a random number generator 103, and a communication unit 104. The radiation imaging apparatus 101b has the same internal arrangement as that of the radiation imaging apparatus 101a.

The detection unit 107 has a two-dimensional pattern (for example, a two-dimensional array pattern) of pixels including switch elements such as TFTs and photoelectric conversion elements. For example, a fluorescence substance that converts radiation into visible light is provided on each photoelectric conversion element. The fluorescence substances convert the radiation that has entered the detection unit 107 into visible light. The converted visible light enters the photoelectric conversion element of each pixel. Each photoelectric conversion element generates charges (an electrical signal) as radiation image data in accordance with visible light.

The imaging control unit 102 performs processing concerning drive control of the detection unit 107, various types of image processes for radiation image data obtained by imaging, saving of radiation image data, determination of the transfer timing of radiation image data, and transfer control of radiation image data.

The imaging control unit 102 includes a drive control unit 105 and a time count control unit 106. The drive control unit 105 performs drive control of the detection unit 107. As described later, the time count control unit 106 is used for synchronization between irradiation with radiation and the drive timing of the detection unit 107. The time count control unit 106 holds an internal timepiece. The time count control unit 106 corrects the time of the internal timepiece with respect to the irradiation control apparatus 120, and controls the drive timing of the detection unit 107 based on the time information of the internal timepiece. The radiation image data generated by the detection unit 107 and processed by the imaging control unit 102 is transferred to an image processing apparatus (not shown) via a network and used for an examination or the like. The communication unit 104 transfers images.

The radiation imaging apparatuses 101*a* and 101*b* and the irradiation control apparatus 120 are connected to each other via a communication network. The communication network includes a network switch 114. Devices connected to each other via the communication network exchange information in the form of messages. Note that the radiation imaging apparatuses 101*a* and 101*b* may be structured to include both wireless and wired communication units and automatically switch communication schemes upon determination of the connection state of each apparatus.

In contrast to this, because the radiation generating apparatus 110 and the irradiation control apparatus 120 are electrically and directly connected to each other without intervention of any communication network, information is directly transferred as electrical signals without being converted into a message form.

As described above, the radiation imaging apparatuses 101*a* and 101*b* each use the time count control unit 106 for synchronization between irradiation with radiation and the drive timing of the detection unit 107. The following are the contents of this operation.

First of all, before an imaging operation, parameters for imaging for moving images (for example, a frame rate and the length of a radiation pulse per frame) are set in advance in each unit of the system. The operator of the radiation imaging system presses the exposure button 115 at the desired timing of imaging. Information indicating that the exposure button 115 has been pressed is transmitted as an electrical signal to the irradiation control apparatus 120. Upon receiving this signal, the irradiation control apparatus 120 generates a message indicating that imaging starts, and exchanges the message with the radiation imaging apparatuses 101*a* and 101*b* via the communication network. This message includes information about the start time of imaging.

After the message indicating that imaging starts is exchanged and the start time of imaging is shared among the radiation imaging apparatuses 101*a* and 101*b* and the irradiation control apparatus 120, the irradiation pulse generating unit 123 in the irradiation control apparatus 120 generates a timing pulse for irradiation with radiation. The time count control unit 122 in the irradiation control apparatus 120 holds information about the progress time. The irradiation pulse generating unit 123 generates a timing pulse based on the time information held by the time count control unit 122. This timing pulse is transmitted to the radiation generating apparatus 110. The radiation generating apparatus 110 then applies radiation 111 in accordance with the timing pulse.

In each of the radiation imaging apparatuses 101*a* and 101*b*, after exchange of a message indicating that imaging starts, the drive control unit 105 in the imaging control unit 102 generates a drive control signal for the detection unit 107, and obtains radiation image data from the detection unit 107. The time count control unit 106 in each of the radiation imaging apparatuses 101*a* and 101*b* holds information about the progress time, and the drive control unit 105 generates a drive control signal based on the time information held by the time count control unit 106.

When the operator of the radiation imaging system 100 stops pressing the exposure button 115 to stop imaging, the irradiation control apparatus 120 stops generating a timing pulse and generates a message indicating that imaging stops. The irradiation control apparatus 120 then exchanges the message with the radiation imaging apparatuses 101*a* and 101*b*.

In the above operation, radiation image data is obtained at the time selected not to overlap any timing pulse for irradiation with radiation. That is, radiation image data is obtained in a time zone different from a time zone of irradiation with radiation. In order to implement this exclusive operation, the time of the time count control unit 122 in the irradiation control apparatus 120 needs to be accurately synchronized with the time of the time count control unit 106 in each of the radiation imaging apparatuses 101*a* and 101*b*.

Figure 2:
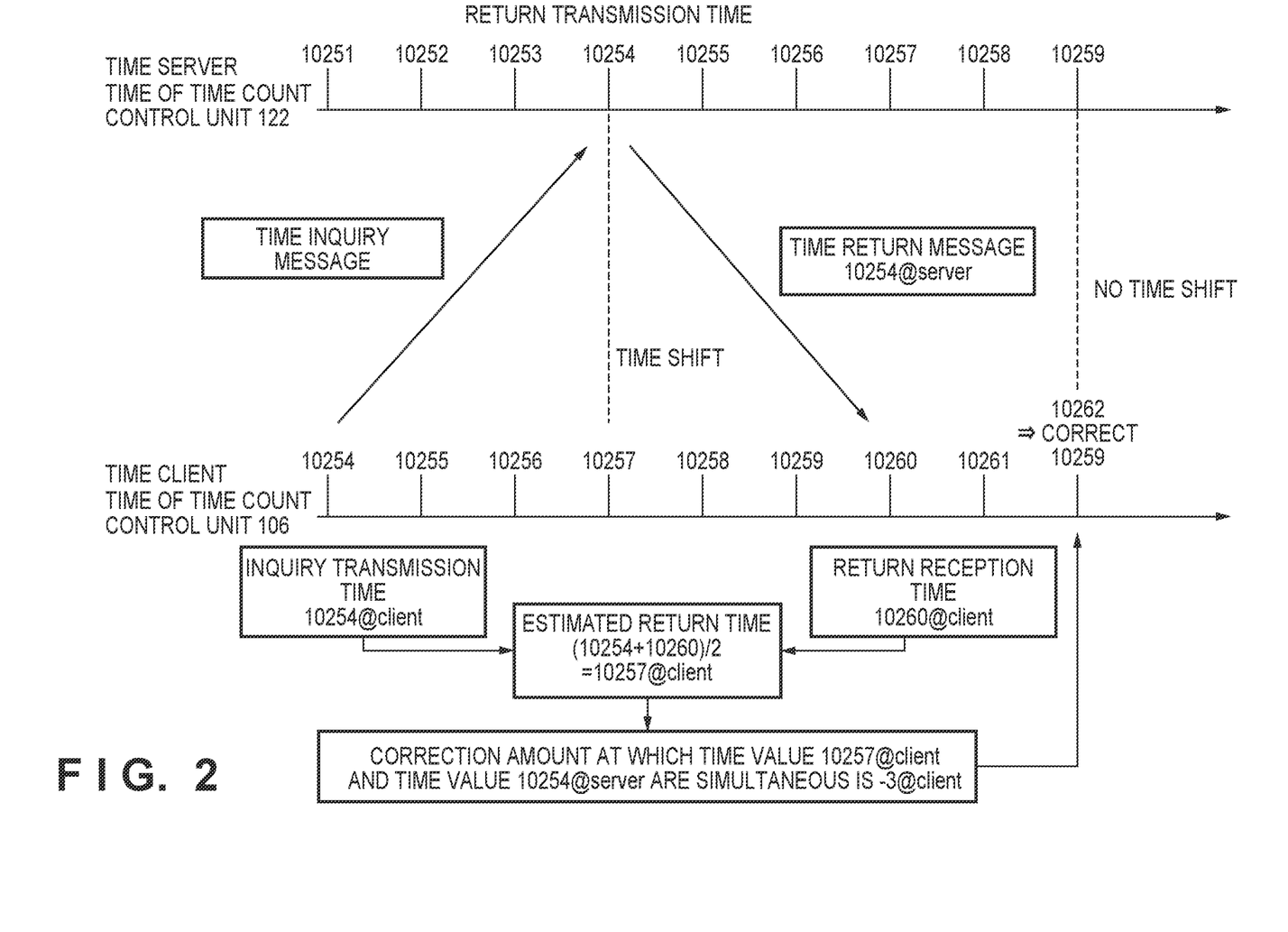
FIG. 2 is a view for explaining a synchronization procedure for time information between apparatuses according to the embodiment.

FIG. 2 is a view for explaining a procedure for synchronization between time information of the time count control unit 106 in each of the radiation imaging apparatuses 101*a* and 101*b* and time information of the time count control unit 122 in the irradiation control apparatus 120. The time count control unit 122 operates as a time server, that is, a reference timepiece, and the time count control unit 106 operates as a time client, that is, "a timepiece that operates following the time server".

First of all, each of the radiation imaging apparatuses 101*a* and 101*b* transmits time inquiry message (time synchronization transmission information) inquiring about the time of the time server via the communication unit 104 to the time count control unit 122. At this time, when the time count control unit 106 of each of the radiation imaging apparatuses 101*a* and 101*b* transmits a message, the time count control unit 106 internally stores time information at the transmission time and transmits the time information. For example, when the time count control unit 106 has transmitted a message at time value 10254 indicated by the timepiece held by the time count control unit 106, the time count control unit 106 stores time value 10254 as an inquiry transmission time in the internal memory and transmits the message.

Upon receiving the time inquiry message from the time count control unit 106 of each of the radiation imaging apparatuses 101*a* and 101*b*, the irradiation control apparatus 120 transmits a time return message (time synchronization return information). That is, like a time client, the time count control unit 122 of the irradiation control apparatus 120 transmits a time return message.

Upon, for example, transmitting time synchronization return information 201 at time value 10254 indicated by the timepiece held by the time count control unit 122, the time count control unit 122 stores time value 10254 as a return transmission time in a time return message (10254@server;

"@server" will indicate the time in the time server hereinafter) and transmits the message.

Each of the radiation imaging apparatuses 101a and 101b receives the time return message transmitted from the irradiation control apparatus 120. At this time, each of the radiation imaging apparatuses 101a and 101b obtains the time return message at the time before correction (return reception time) held by the time count control unit 106 of each of the radiation imaging apparatuses 101a and 101b. For example, as shown in FIG. 2, the time count control unit 106 obtains a time return message at time value 10260 and stores the time value as a return reception time in the internal memory.

Assume that both the communication of a time inquiry message and the communication of a time return message require the same communication time (propagation time). In this case, the time count control unit 106 can estimate the time (estimated return time) when the irradiation control apparatus 120 has transmitted a time return message as the intermediate time between inquiry transmission time 10254 (10254@client; "@client" will indicate the time in the client hereinafter) and return reception time 10260 (10260@client) based on the time of the timepiece held by the time count control unit 106.

That is, the time count control unit 106 can estimate an estimated return time as (10254+10260)/2=10257 (10257@client) by the following averaging operation.

In order to obtain the time shift between each of the radiation imaging apparatuses 101a and 101b and the irradiation control apparatus 120, the time count control unit 106 (client) obtains the difference between the estimated return time in the client and the return transmission time in the irradiation control apparatus 120 (time server). That is, when the time count control unit 106 obtains the difference time (time difference) between the estimated return time (10257@client) and the return transmission time (10254@server), there is a time shift between them. This indicates that the time in each of the radiation imaging apparatuses 101a and 101b has advanced by 10257-10254=3. A correction value that matches time value 10257@client with time value 10254@server is −3@client.

The time count control unit 106 corrects the time value of the timepiece held by the time count control unit 106 based on the obtained time difference, and synchronizes the time in the time count control unit 106 with the time in the time count control unit 122.

The time count control unit 106 corrects estimated return time 10257 (10257@client) in the client by subtracting the difference time (time difference) from the time information of the time count control unit 106 in the client so as to match the estimated return time 10257 (10257@client) with return transmission time 10254 (10254@server) in the time server.

That is, the time count control unit 106 subtracts the correction amount (−3@client) from the time value (10262@client) of the timepiece held by the time count control unit 106 to correct the time value of the timepiece. Referring to FIG. 2, the time value after correction is the time value (10259@client), which matches the time value (10259@server) of the timepiece of the time count control unit 122.

The above arithmetic processing makes it possible to calculate the time difference between the time count control unit 106 and the time count control unit 122. The time count control unit 106 corrects the time information of the time count control unit 106 based on the calculated time difference. This eliminates the time shift between each of the radiation imaging apparatuses 101a and 101b and the irradiation control apparatus 120 (time synchronization state).

In the case shown in FIG. 2, the time count control unit 122 in the irradiation control apparatus 120 serves as a time server, and the time count control unit 106 in each of the radiation imaging apparatuses 101a and 101b serves as a time client. However, the time count control unit 122 and the time count control unit 106 may respectively function as a time client and a time server.

In the case shown in FIG. 2, an estimated return time is obtained based on one inquiry using a combination of time synchronization transmission information 200 and time synchronization return information 201 as a set, and a time correction value (time synchronization correction value) is determined based on the difference time (time difference) between an estimated return time and an inquiry transmission time. In practice, however, because fluctuations can occur in the communication time (propagation time), a time correction value based on a single inquiry can deviate from the true time. Accordingly, it is possible to calculate a time correction value by executing a plurality of inquiries and statistically processing the time differences obtained in correspondence with the respective inquiries.

The radiation imaging system according to this embodiment is configured to transmit, via a network, various information such as radiation image data obtained by imaging, messages exchanged to control the start and end of imaging, and inquiries and returns for time synchronization. In addition, such information includes commands for transmitting preliminary setting information and a message reporting abnormality or normality in each apparatus. These pieces of information transmitted via the network pass through the same medium but differ in how data are communicated (transferred). For example, radiation image data is constituted by a large amount of data as compared with a time synchronization packet, and hence can be transmitted upon being divided into many image data packets.

When a message is transmitted from each of the radiation imaging apparatuses 101a and 101b or the irradiation control apparatus 120, the message arrives first at the network switch 114. The network switch 114 determines the destination of each arrival message and relays (transmits) the message to the corresponding destination.

A single communication channel in a network can handle only a single message at a time and hence cannot simultaneously carry a plurality of messages unless special multiplexing processing is applied to the communication channel. On the other hand, the network switch 114 may simultaneously receive messages addressed to the same destination from a plurality of transmission sources via individual communication channels. In this case, such a situation will be referred to as "collision" of messages.

When messages to be relayed collide, the network switch 114 relays (transmits) one of the colliding messages and, at the same time, stores the other message in the internal storage unit (buffer) of the network switch 114. After transmission completion of the message relayed first, the network switch 114 obtains the other message stored in the storage unit (buffer) and transmits the message to the destination. The network switch 114 operates to solve the collision of messages by delaying one of the messages in the buffer and transmit both the colliding messages to the destinations.

Such a collision solving operation of the network switch 114 has an important function in reducing the possibility of loss of messages in the network. However, this operation can have an influence on time synchronization communication like that described above. This influence will be described with reference to FIG. 3.

Figure 3:
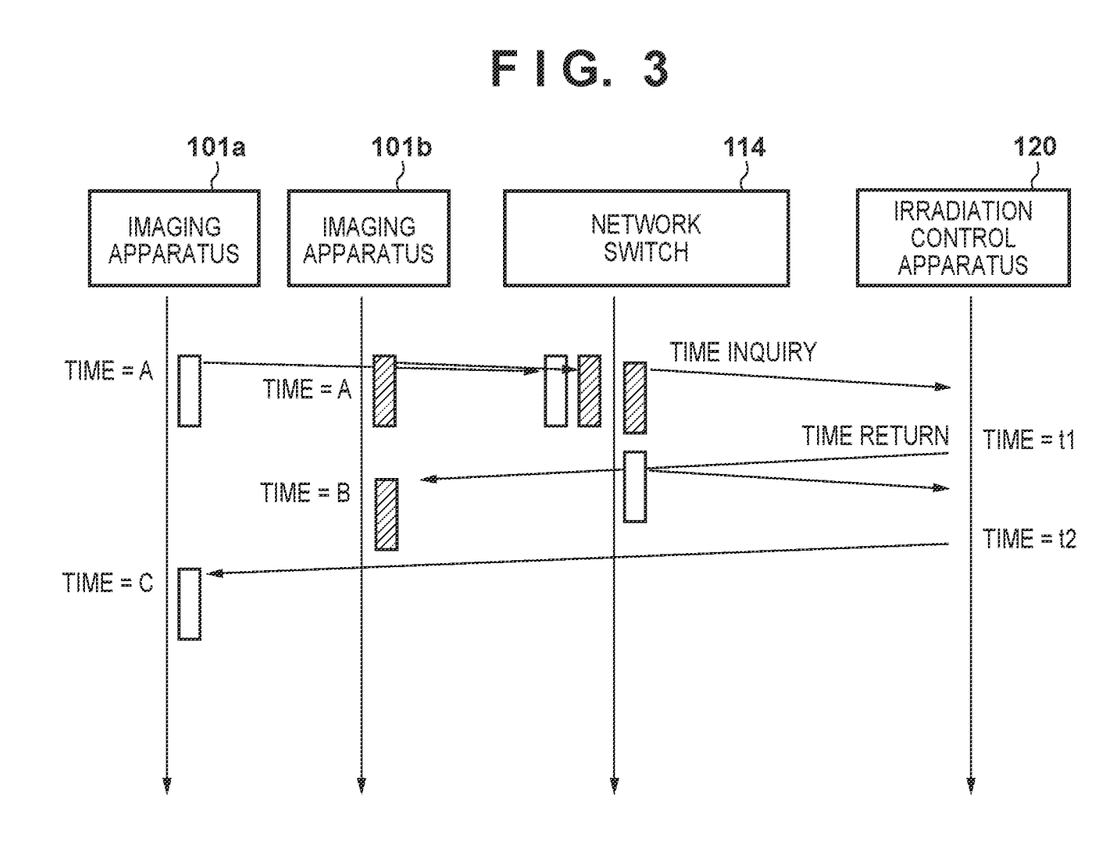
FIG. 3 is a view showing the procedure of communication in each device when time inquiry messages collide with each other.

FIG. 3 is a view showing the flow of communication in each device when time inquiry messages collide with each other. Referring to FIG. 3, the radiation imaging apparatuses 101a and 101b as time clients simultaneously transmit time inquiry messages (inquire about the time) to the irradiation control apparatus 120 as a time server at given time A (inquiry transmission time). For the sake of simple description, it is assumed that the times in the respective apparatuses have already been synchronized, and hence the time difference obtained as a result of inquiries should be zero.

Collision occurs when time inquiry messages simultaneously arrive at the network switch 114. In order to transmit both the time inquiry messages to the irradiation control apparatus 120, the network switch 114 needs to temporarily store one of the time inquiry messages in the storage unit (buffer) and to complete transmission of one time inquiry message first and then transmit the other time inquiry message stored in the buffer upon obtaining the message from the buffer.

In the case shown in FIG. 3, the network switch 114 relays (transmits) first the time inquiry message from the radiation imaging apparatus 101b to the irradiation control apparatus 120, and then relays (transmits) the time inquiry message from the radiation imaging apparatus 101a to the irradiation control apparatus 120 after transmission completion of the message from the radiation imaging apparatus 101b.

The irradiation control apparatus 120 sequentially returns messages in response to the time inquiry messages that arrive sequentially. The irradiation control apparatus 120 returns a message in response to the time inquiry message from the radiation imaging apparatus 101b, which has been processed first, by sending time t1 (return transmission time) over a time return message, and then returns a message in response to the time inquiry message from the radiation imaging apparatus 101a, which has been processed afterward, by sending time t2 (return transmission time) over a time return message.

The time return message arrives at the radiation imaging apparatuses 101a and 101b as if the message were traced back along the route of the time inquiry message. Note that the communication channel in this case is a communication channel that can perform full-duplex communication, that is, can simultaneously forward communication and backward communication. Unlike time inquiry messages, time return messages are sequentially sent out from the irradiation control apparatus 120 onto a single medium, and hence no collision occurs on the network switch 114. These time return messages arrive at the radiation imaging apparatus 101b and the radiation imaging apparatus 101a at time B (return reception time) and time C (return reception time), respectively.

In this case, it is assumed that the times in the respective apparatuses have already been synchronized, and hence the time difference obtained as a result of inquiries should be zero. With regard to the radiation imaging apparatus 101b, if (time A (inquiry transmission time)+time B (return reception time))/2=time t1 (return transmission time), the time difference between the forward path and the backward path in the communication route is zero. As shown in FIG. 3, with regard to the radiation imaging apparatus 101b, because no congestion occurs in the network switch 114, the time taken for propagation in the forward path becomes equal to the time taken for propagation in the backward path. Therefore, the above equation holds.

With regard to the radiation imaging apparatus 101a, considering the relationship between (time A (inquiry transmission time)+time C (return reception time))/2 and time t2 (return transmission time), because the propagation time in the forward path is prolonged by the time taken for collision solution, these times are not equal. When the time in the radiation imaging apparatus 101a is corrected in the manner described with reference to FIG. 2, the actual times, which have been synchronized with each other at first in the situation shown in FIG. 3, are corrected so as to be shifted from each other. In addition, assume that the inquiry interval in the radiation imaging apparatus 101a is equal to that in the radiation imaging apparatus 101b. In this case, once messages collide with each other as in FIG. 3, the same situation repeatedly occurs afterward.

In order to prevent the occurrence of a time difference due to congestion caused by message collision, the system according to this embodiment is configured to adjust the transmission intervals of time inquiry messages so as to prevent message collision. More specifically, making the transmission intervals of time inquiry messages have a random nature will prevent repetitive collision of time inquiry messages.

In the radiation imaging system 100 according to this embodiment, each of the radiation imaging apparatuses 101a and 101b has identification information (ID) unique to the apparatus. This information may be the production serial number of each apparatus or a network address such as an IP address or a MAC address. In addition, the radiation imaging apparatuses 101a and 101b each include the random number generator 103. Each random number generator 103 operates based on identification information (ID) unique to a radiation imaging apparatus (time client) and is configured to generate random number sequences different from each other between a plurality of time clients. Each radiation imaging apparatus adjusts the transmission intervals of time inquiry messages to irregular intervals by adding outputs from the random number generator 103 to standard transmission intervals which are equal intervals, and transmits time inquiry messages.

Figure 4:
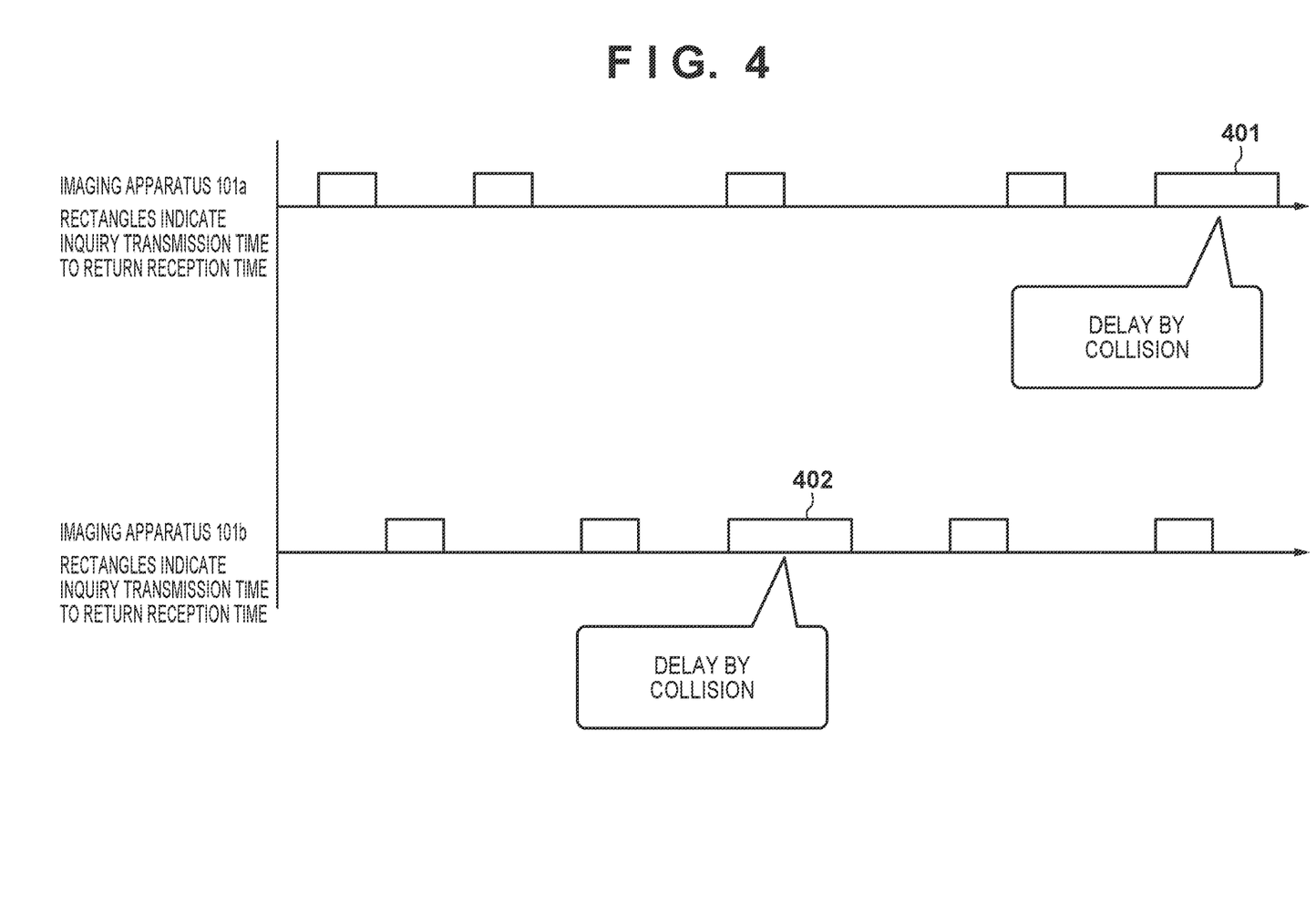
FIG. 4 is a view showing how each apparatus transmits time inquiry messages adjusted to irregular intervals.

FIG. 4 is a view showing how each apparatus transmits time inquiry messages adjusted to irregular intervals. Referring to FIG. 4, each of the radiation imaging apparatuses 101a and 101b independently transmits time inquiry messages. Referring to FIG. 4, each rectangular portion indicates the time from an inquiry transmission time to a return reception time. The intervals of the respective rectangles are adjusted to irregular intervals by using outputs from the random number generator 103. A message collision has occurred between a rectangle 401 and a rectangle 402. At this time, a return from the irradiation control apparatus 120 is sometimes delayed (referring to FIG. 4, the horizontally long rectangles 401 and 402 indicate that long times have been required as compared with other rectangles). However, because different inquiry intervals are set in the respective apparatuses, even if a collision occurs, this situation does not continue.

Figure 5:
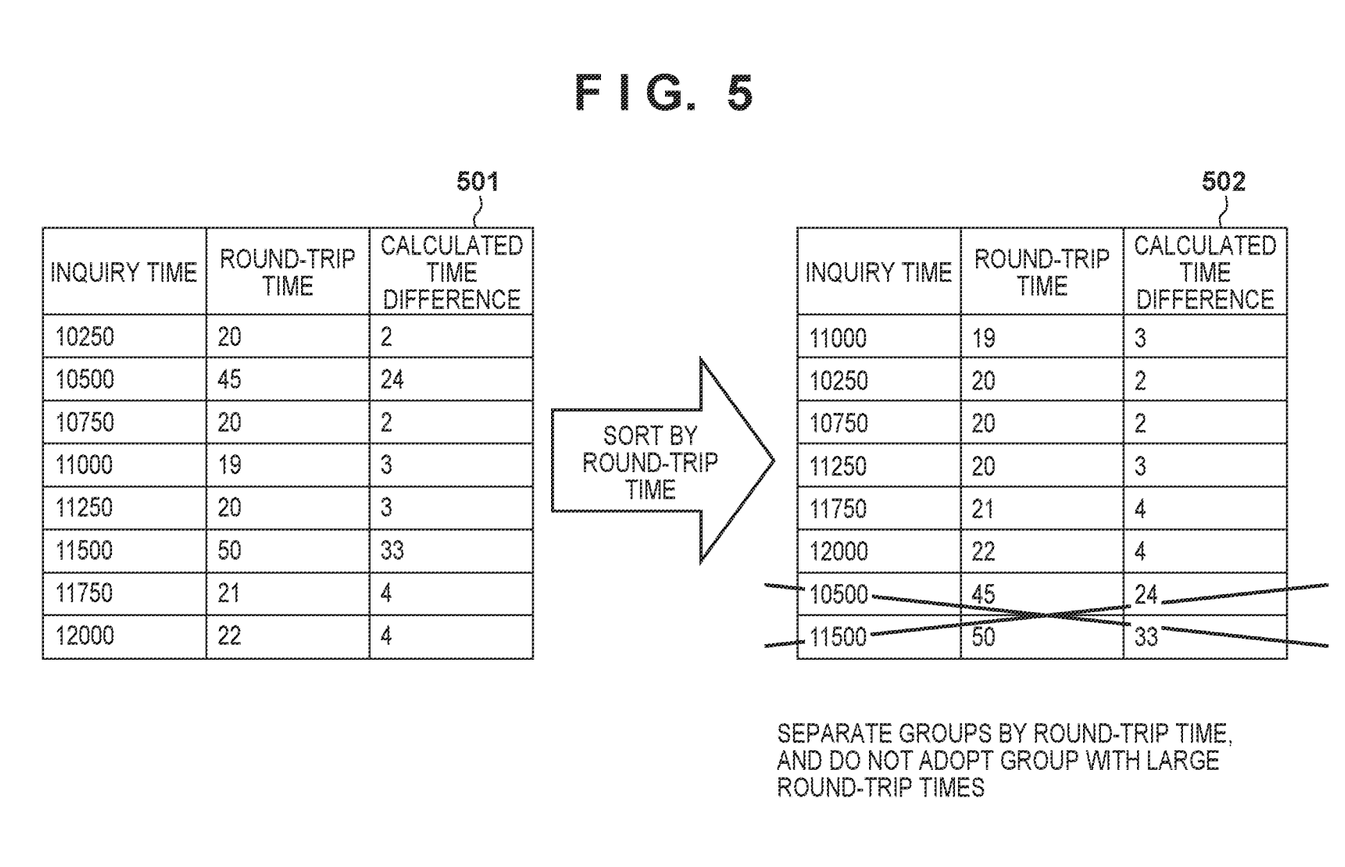
FIG. 5 is a view for explaining a process of excluding inquiry results at the time of collision.

For example, a table 501 in FIG. 5 indicates a summary of results obtained by executing inquiry a plurality of times in the radiation imaging system 100 according to this embodiment. In the table 501, "round-trip time" indicates a time from an inquiry transmission time to a return reception time, and "calculated time difference" indicates the difference time between an estimated return time and a return transmission time.

A table 502 in FIG. 5 is obtained by grouping (sorting) the results in the table 501 in FIG. 5 according to communication round-trip times. This indicates a correlation between the magnitudes of the round-trip times and the calculated time differences. That is, a message collision prolongs the round-trip time, and the apparent time difference increases at this time. Based on this correlation, a group of samples with large round-trip times due to the occurrence of message collisions (samples with round-trip times of 45 and 50) is separated, and time differences are corrected with respect to the remaining samples. This makes it possible to implement time synchronization with reduced influences of communication collisions. If the round-trip time from the inquiry transmission time of a message to the return reception time when a return message is received is longer than a predetermined time (samples with round-trip times of 45 and 50), the time count control unit 106 does not correct the time information of the internal timepiece with respect to the return message.

When the transmission intervals in the radiation imaging apparatuses 101a and 101b are equal intervals, samples cannot be grouped (sorted) even by generating a table like the table 501 in FIG. 5 because of constant round-trip times. Accordingly, samples with the occurrence of message collisions cannot be specified. This may lead to wrong correction.

In contrast, the radiation imaging system 100 according to this embodiment is configured to adjust the transmission intervals of time inquiry messages to irregular intervals by adding outputs from the random number generator 103 to standard transmission intervals (equal intervals). This may eliminate the possibility of collision among all samples. This makes it possible to neglect the possibility that collision states will occupy all the samples. Accordingly, even if round-trip times fall within a predetermined range and samples cannot be divided into groups, it is possible to set all the samples as targets for time correction while regarding them without any collision.

The radiation imaging system 100 according to this embodiment can suppress a reduction in the accuracy of time synchronization by setting the transmission intervals of time inquiry messages to irregular intervals to reduce the possibility of collision among time inquiry messages by using the random numbers generated based on identification information (ID) unique to each radiation imaging apparatus. This enables time synchronization with higher accuracy even when transferring image data from a plurality of radiation imaging apparatuses (time clients).

Second Embodiment

An arrangement according to the second embodiment which is configured to adjust the transmission intervals of time inquiry messages will be described. The arrangement of a radiation imaging system 100 is the same as that of the first embodiment, and includes radiation imaging apparatuses 101a and 101b, a radiation generating apparatus 110, and an irradiation control apparatus 120 that controls the radiation generating apparatus 110. Other arrangements, for example, an arrangement concerning the start and end of imaging, and the basic principle of time synchronization are the same as those of the first embodiment, and hence a description will be omitted.

Figure 6:
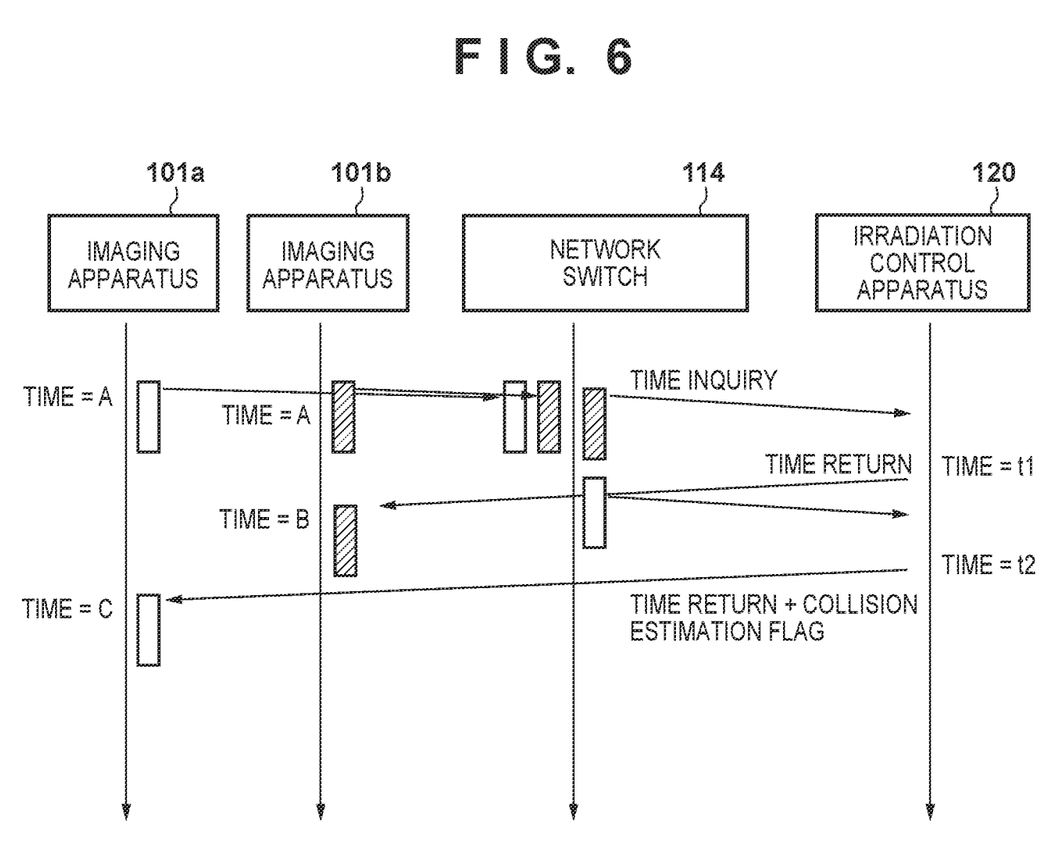
FIG. 6 is a view showing the procedure of communication in each device at the time of collision of time inquiry messages according to the second embodiment.

FIG. 6 is a view showing the procedure of communication in each device at the time of collision of time inquiry messages according to the second embodiment. FIG. 6 corresponds to FIG. 3 described in the first embodiment. The processing shown in FIG. 6 differs from the processing according to the first embodiment in that additional information is added to a time return message to the radiation imaging apparatus 101a to adjust the transmission intervals of time inquiry messages. The irradiation control apparatus 120 adds such additional information to a time return message upon estimating (determining) that time inquiry messages have collided with each other. This additional information will be referred to as "a collision estimation flag".

The irradiation control apparatus 120 sequentially returns time return messages in response to time inquiry messages sent from the radiation imaging apparatuses 101a and 101b. At this time, if the irradiation control apparatus 120 receives time inquiry messages from different transmission sources in a row within a predetermined time, these time inquiry messages may have collided with each other midway along the communication route. In this case, the time inquiry message that has arrived later, in particular, poses a problem. If the irradiation control apparatus 120 returns a time return message as it is, the radiation imaging apparatus 101a that has received the time return message is likely to perform wrong time correction.

When a plurality of messages have arrived within a predetermined time, a time count control unit 122 of the irradiation control apparatus 120 outputs, to a communication unit 121, collision estimation information generated with respect to the message that has arrived later from the radiation imaging apparatus. In such a case, when a plurality of messages have arrived within the predetermined time, the time count control unit 122 of the irradiation control apparatus 120 according to this embodiment estimates the occurrence of a collision and generates a message (time return message) to which a collision estimation flag is added as collision estimation information. Alternatively, the time count control unit 122 generates a collision estimation message as collision estimation information. The time count control unit 122 then returns the message to which the collision estimation flag is added (time return message) or the generated collision estimation message out of the plurality of messages to the time client as the transmission source that has transmitted the message that arrived later.

Figure 7:
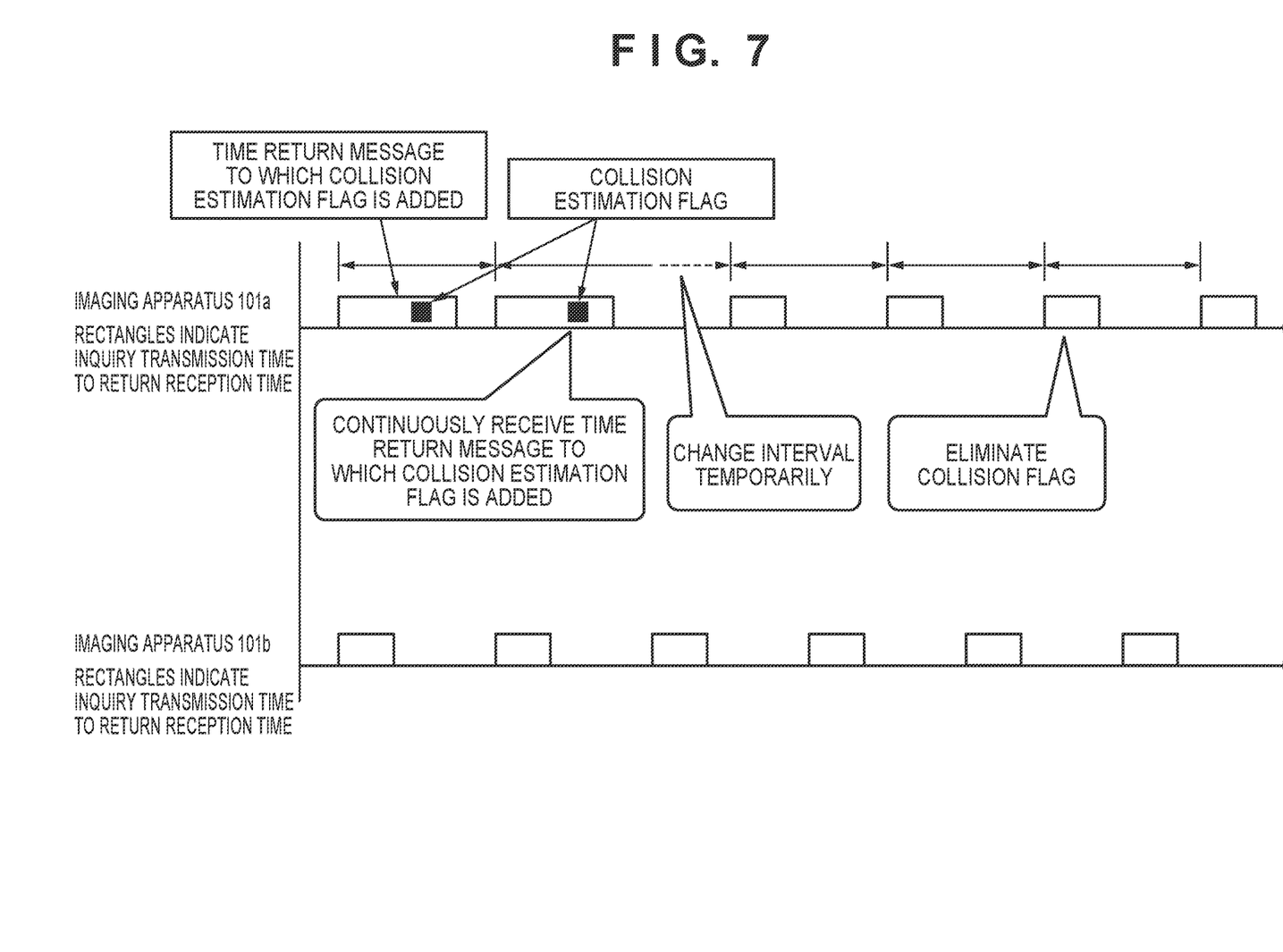
FIG. 7 is a view for explaining a process of adjusting the transmission intervals of time inquiry messages upon detection of collision.

FIG. 7 is a view for explaining a process of adjusting the transmission intervals of time inquiry messages upon detection of collision. FIG. 7 shows a case in which a message to which a collision estimation flag is added is returned. However, this applies to a case in which a collision estimation message is returned. When a plurality of time inquiry messages have arrived within a predetermined time, the time count control unit 122 of the irradiation control apparatus 120 generates and returns a time return message to which a collision estimation flag is added in response to the time inquiry message that has arrived later from the radiation imaging apparatus 101a.

When a collision estimation flag is added to a time return message, a time count control unit 106 of the radiation imaging apparatus 101a can avoid using the corresponding time return message as a reference for time synchronization. That is, upon receiving collision estimation information (a time return message to which a collision estimation flag is added or a collision estimation message), the time count control unit 106 of the radiation imaging apparatus 101a (time client) does not correct the time information of the internal timepiece based on the time information of the irradiation control apparatus 120 (time server).

When a collision estimation flag is added to a time return message, the time count control unit 106 of the radiation imaging apparatus 101a temporarily adjusts the transmission intervals of time inquiry messages to irregular intervals (prolongs a transmission interval in the case shown in FIG. 7). The time count control unit 106 may change a transmission interval only once or may change transmission intervals in a preset number of times of communication.

After a transmission interval is changed only once or transmission intervals are changed in a preset number of times of communication, the transmission intervals of messages are returned to the initial intervals. Subsequently, the radiation imaging apparatus 101a continues inquiry at the initial transmission intervals. Changing the transmission intervals will solve persistent collisions of time inquiries from the radiation imaging apparatus 101a and the radiation imaging apparatus 101b. Subsequently, the radiation imaging apparatus 101a can receive time return messages to which no collision estimation flag is added, and the time count control unit 106 can perform correct time difference estimation and time correction based on these messages.

Transmission intervals may be changed by, for example, adding outputs from the random number generator 103 to standard transmission intervals which are equal intervals as in the first embodiment or adding preset additional times for adjustment to the standard transmission intervals.

In this embodiment, upon estimating (determining) the occurrence of a collision, in processing time inquiry messages, based on the arrival timings of a plurality of inquiry messages that have arrived within a predetermined time, the irradiation control apparatus 120 generates a time return message to which a collision estimation flag is added and returns the message to the radiation imaging apparatus. When a collision estimation flag is added to a time return message, the radiation imaging apparatus avoids using the time return message to which the collision estimation flag is added as a reference for time synchronization. That is, the time count control unit 106 eliminates collisions between time inquiry messages by discarding time information with low reliability set for a time return message and changing the transmission intervals of time inquiry messages.

This embodiment has exemplified the case in which a collision estimation flag is configured to be added to (contained in) a time return message. However, this is not exhaustive. For example, when a plurality of time inquiry messages have arrived within a predetermined time, the irradiation control apparatus 120 may generate a collision estimation notification message in response to the time inquiry message from the radiation imaging apparatus 101a, which has arrived later, and transmit the generated message to the radiation imaging apparatus 101a, in addition to a time return message. Alternatively, when the occurrence of collision between time inquiry messages is estimated, the irradiation control apparatus 120 may generate only a collision estimation notification message and transmit it to the radiation imaging apparatus 101a, or may not transmit any time return message.

In the radiation imaging system 100 according to this embodiment, when the occurrence of a collision between time inquiry messages is estimated, the irradiation control apparatus 120 generates a collision estimation flag or collision estimation notification message and transmits it to a radiation imaging apparatus (time client). The radiation imaging apparatus (time client) eliminates collisions between time inquiry messages by changing the transmission intervals of time inquiry messages. Reducing the possibility of collision between time inquiry messages can suppress a decrease in the accuracy of time synchronization. Accordingly, even when a plurality of radiation imaging apparatuses (time clients) transfer image data, it is possible to perform time synchronization with higher accuracy.

Although the embodiments (the first and second embodiments) of the present invention have been described above, it is obvious that the present invention is not limited to these embodiments, and various changes and modifications can be made within the spirit and scope of the invention.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-245378, filed Dec. 27, 2018, which is hereby incorporated by reference herein in its entirety.

What is claimed is:

1. A time synchronization system including at least one time server and a plurality of time clients connected to each other via a network, the time client comprising:
one or more memories that store instructions; and
one or more processors that execute the instructions to function as:
a communication unit configured to obtain time information of the time server by transmitting/receiving messages to/from the time server; and
a time count control unit configured to synchronize time information of an internal timepiece with the time information of the time server,
wherein the time count control unit controls transmission of the messages by adjusting transmission intervals of the messages to irregular intervals,
wherein the time count control unit estimates, based on an inquiry transmission time of the message and a return reception time when a time client has received a return message storing a return transmission time in response to the message, an estimated return time when the time server has returned the return message, and wherein the time count control unit obtains a time correction value from a difference time between the estimated return time and the return transmission time, and corrects the time information of the internal timepiece by using the time correction value.

2. The system according to claim 1, wherein the one or more processors further execute the instructions to function as a random number generating unit, and wherein the time count control unit adjusts the transmission intervals to the irregular intervals by adding outputs from the random number generating unit to standard transmission intervals which are equal intervals.

3. The system according to claim 2, wherein the random number generating unit operates based on identification information unique to the time client and is configured to generate random number sequences different from each other between the plurality of time clients.

4. The system according to claim 1, wherein the time count control unit avoids correcting the time information of the internal timepiece with respect to the return message when a round-trip time from the inquiry transmission time of the message to the return reception time when the return message is received is longer than a predetermined time.

5. A time synchronization system including at least one time server and a plurality of time clients connected to each other via a network, the time server comprising:
one or more first memories that store first instructions; and
one or more first processors that execute the first instructions to function as:
a communication unit configured to transmit time information of an internal timepiece upon transmitting/receiving messages to/from the plurality of time clients; and
a time count control unit configured to output, when a plurality of messages have arrived within a predetermined time, via the communication unit, collision estimation information generated with respect to a message from a time client which has arrived later, and the time client comprising:
one or more second memories that store second instructions; and
one or more second processors that execute the second instructions to function as:
a time count control unit configured to synchronize the time information of the internal timepiece with time information of the time server which is obtained by transmitting a message, wherein the time count control unit of the time client adjusts transmission intervals of the messages to irregular intervals and controls transmission of the messages upon receiving the collision estimation information.

6. The system according to claim 5, wherein the time count control unit of the time client avoids correcting the time information of the internal timepiece based on the time information of the time server upon receiving the collision estimation information.

7. The system according to claim 5, wherein the time count control unit of the time server estimates that a collision has occurred and generates a message to which a collision estimation flag as the collision estimation information is added when a plurality of messages have arrived within the predetermined time.

8. The system according to claim 5, wherein the time count control unit of the time server estimates that a collision has occurred and generates a collision estimation message as the collision estimation information when the plurality of messages have arrived within the predetermined time.

9. The system according to claim 8, wherein the time count control unit of the time server returns a message to which a collision estimation flag is added or the generated collision estimation message to a time client as a transmission source which has transmitted a message which has arrived later out of the plurality of messages.

10. A radiation imaging system including a plurality of radiation imaging apparatuses functioning as time clients and an irradiation control apparatus functioning as a time server and configured to control a radiation generating apparatus, the radiation imaging apparatus comprising:
one or more memories that store instructions; and
one or more processors that execute the instructions to function as:
a communication unit configured to obtain time information of the irradiation control apparatus by transmitting/receiving messages to/from the time server; and
a time count control unit configured to synchronize time information of an internal timepiece with time information of the irradiation control apparatus, wherein the time count control unit controls transmission of the messages by adjusting transmission intervals of the messages to irregular intervals, wherein the time count control unit estimates, based on an inquiry transmission time of the message and a return reception time when a time client has received a return message storing a return transmission time in response to the message, an estimated return time when the time server has returned the return message, and wherein the time count control unit obtains a time correction value from a difference time between the estimated return time and the return transmission time, and corrects the time information of the internal timepiece by using the time correction value.

11. A radiation imaging system including a plurality of radiation imaging apparatuses functioning as time clients and an irradiation control apparatus functioning as a time server and configured to control a radiation generating apparatus, the irradiation control apparatus comprising:
one or more first memories that store first instructions; and
one or more first processors that execute the first instructions to function as:
a communication unit configured to transmit time information of an internal timepiece by transmitting/receiving messages to/from the plurality of radiation imaging apparatuses; and
a time count control unit configured to output, when a plurality of messages have arrived within a predetermined time, via the communication unit, collision estimation information generated with respect to a message from a radiation imaging apparatus which has arrived later, and the radiation imaging apparatus comprising:
one or more second memories that store second instructions; and
one or more second processors that execute the second instructions to function as:
a time count control unit configured to synchronize the time information of the internal timepiece with time information of the irradiation control apparatus which is obtained by transmitting a message,
wherein the time count control unit of the radiation imaging apparatus adjusts transmission intervals of the messages to irregular intervals and controls transmission of the messages upon receiving the collision estimation information.

12. A method of controlling a time synchronization system including at least one time server and a plurality of time clients connected to each other via a network, the method comprising: in the time client,
obtaining time information of the time server by transmitting/receiving messages to/from the time server; and
synchronizing time information of an internal timepiece with the time information of the time server,
wherein in synchronizing the time information, transmission of the messages is controlled by adjusting transmission intervals of the messages to irregular intervals,
wherein in synchronizing the time information, based on an inquiry transmission time of the message and a return reception time when a time client has received a return message storing a return transmission time in response to the message, an estimated return time is estimated when the time server has returned the return message, and
wherein in synchronizing the time information, a time correction value is obtained from a difference time between the estimated return time and the return transmission time, and the time information of the internal timepiece is corrected by using the time correction value.

13. A method of controlling a time synchronization system including at least one time server and a plurality of time clients connected to each other via a network, the method comprising:
in the time server,
transmitting time information of an internal timepiece upon transmitting/receiving messages to/from the plurality of time clients; and
when a plurality of messages have arrived within a predetermined time, outputting, via a communication unit, collision estimation information generated with respect to a message from a time client which has arrived later, and
in the time client,
synchronizing the time information of the internal timepiece with time information of the time server,
wherein in synchronizing the time information in the time client, transmission intervals of the messages are adjusted to irregular intervals and transmission of the messages is controlled upon reception of the collision estimation information.

14. A radiation imaging apparatus functioning as a time client and configured to communicate with an irradiation control apparatus functioning as a time server, comprising:
one or more memories that store instructions, and
one or more processors that execute the instructions to function as:
a communication unit configured to obtain time information of the irradiation control apparatus by transmitting/receiving messages to/from the time server; and
a time count control unit configured to synchronize time information of an internal timepiece with the time information of the irradiation control apparatus,
wherein the time count control unit controls transmission of the messages by adjusting transmission intervals of the messages to irregular intervals,
wherein the time count control unit estimates, based on an inquiry transmission time of a message and a return reception time when a time client has received a return message storing a return transmission time in response to the message, an estimated return time when the time server has returned the return message, and
wherein the time count control unit obtains a time correction value from a difference time between the estimated return time and the return transmission time, and corrects the time information of the internal timepiece by using the time correction value.

15. A radiation imaging apparatus functioning as a time client and configured to communicate with an irradiation control apparatus functioning as a time server, comprising:
one or more memories that store instructions; and
one or more processors that execute the instructions to function as:
a time count control unit configured to synchronize time information of an internal timepiece with time information of the irradiation control apparatus, which is obtained by transmitting a message,
wherein the time count control unit of the radiation imaging apparatus adjusts transmission intervals of messages to irregular intervals and controls transmission of the messages upon receiving collision estimation information which is output from the irradiation control apparatus, and when a plurality of messages have arrived to the irradiation control apparatus within a predetermined time, which is generated in the irradiation control apparatus with respect to a message which has arrived later.

* * * * *